US008629140B2

(12) United States Patent
Chen et al.

(10) Patent No.: US 8,629,140 B2
(45) Date of Patent: Jan. 14, 2014

(54) HYPOTENSIVE LIPID AND TIMOLOL COMPOSITIONS AND METHODS OF USING SAME

(75) Inventors: June Chen, San Juan Capistrano, CA (US); David F. Woodward, Lake Forest, CA (US); Alexander B. Kharlamb, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 1148 days.

(21) Appl. No.: 10/153,043

(22) Filed: May 22, 2002

(65) Prior Publication Data

US 2003/0069286 A1    Apr. 10, 2003

Related U.S. Application Data

(60) Provisional application No. 60/294,845, filed on May 31, 2001.

(51) Int. Cl.
*A61K 31/215* (2006.01)
*A61K 31/535* (2006.01)

(52) U.S. Cl.
USPC .................... 514/231.5; 514/530; 514/913

(58) Field of Classification Search
USPC ............... 514/231.5, 530, 913, 573
See application file for complete search history.

(56) References Cited

U.S. PATENT DOCUMENTS

| | | | |
|---|---|---|---|
| 4,599,353 A | 7/1986 | Bito | |
| 4,994,274 A | 2/1991 | Chan et al. | |
| 5,028,624 A | 7/1991 | Chan et al. | |
| 5,034,413 A | 7/1991 | Chan et al. | |
| 5,688,819 A | 11/1997 | Woodward et al. | |
| 6,051,576 A * | 4/2000 | Ashton et al. ................ | 514/255 |
| 6,184,250 B1 | 2/2001 | Klimko | |
| 6,248,735 B1 | 6/2001 | Baldwin | |

FOREIGN PATENT DOCUMENTS

| | | |
|---|---|---|
| EP | 0 286 903 A | 10/1988 |
| EP | 0364417 B1 | 4/1990 |
| EP | 0458590 | 11/1991 |
| EP | 0509752 | 10/1992 |
| EP | 0590972 | 4/1994 |
| EP | 1057486 | 6/2000 |
| EP | 0660716 | 11/2001 |
| WO | WO 97/30710 A | 8/1997 |
| WO | 98-25620 | 6/1998 |
| WO | 00-04898 | 2/2000 |
| WO | 00-54810 | 9/2000 |

OTHER PUBLICATIONS

Starr, "Further Studies on the Effect of Prostaglandin on Intraocular Pressure in the Rabbit", Exp. Eye Res. 1971, 11, pp. 170-177.
Bito, Biological Protection with Prostaglandins, 1985, pp. 231-252.
Bito, Glaucoma: Applied Pharmacology in Medical Treatment, 1984, pp. 477-505.
Nilsson et al, Invest. Ophthalmol. Vis. Sci. 28 (suppl), 284 (1987).
Bito, Arch. Ophthalmol. 105, 1036-1039(1987).
Prodrug 5, 3 (1989).
Resul, B. et al., "Structure-Activity Relationships and Receptor Profiles of Some Ocular Hypotensive Prostanoids", *Survey of Ophthalmology*, vol. 41, Supplement 2, pp. S47-S52, Feb. 1997.
Alexander, C., et al., "Prostaglandin Analog Treatment of Glaucoma and Ocular Hypertension", *The Annals of Pharmacotherapy*, vol. 36, pp. 504-511, Mar. 2002.
A. Hommer, 2001, Bimatoprost: Erste Wirksubstanz Einer Neuen Stoffklasse, Der Prostamide Fur Die Glaukombehandlung, Spektrum Augenheilkd, 15, 146-149.
Achim Krauss, 2004, Update on the Mechanism of Action of Bimatoprost: A Review and Discussion of New Evidence, Surv. Ophthalmol., 49 (Supp. 1), S5-S11.
Dan Eisenberg, 2002, Bimatoprost and Travoprost: A Review of Recent Studies of Two New Glaucoma Drugs, Survey of Ophthalmology, 47 (1), S105-S115.
David Woodward, Jan. 24, 2003, Pharmacological Characterization of a Novel Antiglaucoma Agent, Bimatoprost (AGN 192024), J. Pharmacol. Exp. Ther., 305 (2), 772-785.
G.C. Chiou, 1990, Development of D-Timolol for the Treatment of Glaucoma and Ocular Hypertension, J. Ocul. Pharmacol., 6 (1), 67-74.
Gerald Bean, 2008, Commercially Available Prostaglandin Analogs for the Reduction of Intraocular Pressure: Similarities and Differences, Survey of Ophthalmology, 53 (Supp. 1), S69-S84.
Harvey Dubiner, 2001, Efficacy and Safety of Bimatoprost in Patients With Elevated Intraocular Pressure: a 30-Day Comparison With Latanoprost, Surv. Ophthalmol, 45 (4), S353-S560.
Junichi Komoto, Feb. 21, 2006, Prostaglandin $F2\alpha$ Formation From Prostaglandin H2 by Prostaglandin F Synthase (PGFS): Crystal Stucture of PGFS Containing Bimatoprost, American Chemical Society, 45 (7), 1987-1996.
Kirk Maxey, Aug. 2002, he Hydrolysis of Bimatoprost in Corneal Tissue Generates a Potent Prostanoid FP Receptor Agonist, Survey of Ophthalmology, 47 (Supp. 1), S34-S40.
L.A. Sorbera, 2001, Bimatoprost, Drugs of the Future, 26 (5), 433-439.
Lill-Inger Larsson, 2001, The Effect on Diurnal Intraocular Pressure of the Fixed Combination of Latanoprost 0.005% and Timolol 0.5% in Patients With Ocular Hypertension, Acta Ophthalmol. Scand., 79, 125-128.
Louis Cantor, 2001, Bimatoprost: A Member of a New Class of Agents, The Prostamides, for Glaucoma Management, Exp. Opin. Invest. Drugs, 10 (4), 721-731.
Najam Sharif, 2001, Bimatoprost and Its Free Acid Are Prostaglandin FP Receptor Agonists, European Journal of Pharmacology, 432, 211-213.
Najam Sharif, 2003, Bimatoprost (Lumigan®) is an Agonist At the Cloned Human Ocular FP Prostaglandin Receptor : Real-Time FLIPR-Based Intracellular Ca2+ Mobilization Studies, Prostaglandins, Leukotrienes and Essential Fatty Acids, 68, 27-33.
Takashi Ota, 2005, The Effects of Prostaglandin Analogues on IOP in Prostanoid FP-Receptor-Deficient Mice, Invest. Ophthalmol. Vis. Sci., 46, 4159-4163.

\* cited by examiner

*Primary Examiner* — Zohreh Fay

(74) *Attorney, Agent, or Firm* — John E. Wurst

(57) ABSTRACT

New compositions for and methods of treating ocular hypertension provide for effective treatment of ocular hypertension often using reduced concentrations of active components. Such compositions include a timolol component and a hypotensive lipid component. The present compositions and methods are relatively straightforward, can be easily produced, for example, using conventional manufacturing techniques, and can be easily and conveniently practiced, for example, using application or administration techniques or methodologies which are substantially similar to those employed with prior compositions used to treat ocular hypertension.

4 Claims, 2 Drawing Sheets

HYPOTENSIVE LIPID AND TIMOLOL COMPOSITIONS AND METHODS OF USING SAME

RELATED APPLICATION

This application claims the benefit of U.S. provisional application Serial No. 60/294,845 filed May 31, 2001, the disclosure of which is incorporated in its entirety herein by reference.

BACKGROUND OF THE INVENTION

The present invention relates to compositions useful for and methods of treating ocular hypertension. More particularly, the invention relates to such compositions and methods which effectively treat ocular hypertension, for example, reduce or at least maintain intraocular pressure and preferably provide enhanced benefits and/or have reduced side effects relative to other compositions and methods.

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical b-adrenoreceptor antagonists have traditionally been the drugs of choice for treating glaucoma.

Prostaglandins were earlier regarded as potent ocular hypertensives; however, evidence accumulated in the last two decades shows that some prostaglandins are highly effective ocular hypotensive agents and are ideally suited for the long-term medical management of glaucoma. (See, for example, Starr, M. S. *Exp. Eye Res.* 1971, 11, pp. 170-177; Bito, L. Z. *Biological Protection with Prostaglandins* Cohen, M. M., ed., Boca Raton, Fla., CRC Press Inc., 1985, pp. 231-252; and Bito, L. Z., *Applied Pharmacology in the Medical Treatment of Glaucomas* Drance, S. M. and Neufeld, A. H. eds., New York, Grune & Stratton, 1984, pp. 477-505). Such prostaglandins include $PGF_{2\alpha}$, $PGF_{1\alpha}$, $PGE_2$, and certain lipid-soluble esters, such as $C_1$ to $C_5$ alkyl esters, e.g. 1-isopropyl ester, of such compounds.

In the U.S. Pat. No. 4,599,353 certain prostaglandins, in particular $PGE_2$ and PGF2a and the $C_1$ to $C_5$ alkyl esters of the latter compound, were reported to possess ocular hypotensive activity and were recommended for use in glaucoma management.

Although the precise mechanism is not yet known, recent experimental results indicate that the prostaglandin-induced reduction in intraocular pressure results from increased uveoscleral outflow [Nilsson et al., *Invest. Ophthalmol. Vis. Sci.* 28(suppl), 284 (1987)].

The isopropyl ester of $PGF_{2\alpha}$ has been shown to have significantly greater hypotensive potency than the parent compound, which was attributed to its more effective penetration through the cornea. In 1987 this compound was described as "the most potent ocular hypotensive agent ever reported." [See, for example, Bito, L. Z., *Arch. Ophthalmol.* 105, 1036 (1987), and Siebold et al., *Prodrug* 5, 3 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g. its 1-isopropyl ester, in humans. The clinical potential of prostaglandins in the management of conditions associated with increased ocular pressure, e.g. glaucoma, is greatly limited by these side effects.

Certain phenyl and phenoxy mono, tri and tetra nor prostaglandins and their 1-esters are disclosed in European Patent Application 0,364,417 as useful in the treatment of glaucoma or ocular hypertension.

In a series of United States patent applications assigned to Allergan, Inc. prostaglandin esters with increased ocular hypotensive activity accompanied with no or substantially reduced side-effects are disclosed. U.S. Pat. application Ser. No. (USSN) 386,835 (filed Jul. 27, 1989), relates to certain 11-acyl-prostaglandins, such as 11-pivaloyl, 11-acetyl, 11-isobutyryl, 11-valeryl, and 11-isovaleryl $PGF_{2\alpha}$. Intraocular pressure reducing 15-acyl prostaglandins are disclosed in 3U.S. Ser. No. 357,394 (filed May 25, 1989). Similarly, 11,15-9,15- and 9,11-diesters of prostaglandins, for example 11,15-dipivaloyl $PGF_{2\alpha}$ are known to have ocular hypotensive activity. See U.S. Ser. No. 385,645 filed Jul. 27, 1990, now U.S. Pat. No. 4,494,274; 584,370 which is a continuation of U.S. Ser. No. 386,312, and U.S. Ser. No. 585,284, now U.S. Pat. No. 5,034,413 which is a continuation of U.S. Ser. No. 386,834, where the parent applications were filed on Jul. 27, 1989. The disclosures of these patent applications are hereby expressly incorporated by reference.

Woodward et al U.S. Pat. No. 5,688,819 discloses certain cyclopentane heptanoic acid, 2-cycloalkyl or arylalkyl compounds as ocular hypotensives. These compounds, which can properly be characterized as hypotensive lipids, are effective in treating ocular hypertension. The disclosure of this U.S. Patent is hereby expressly incorporated by reference.

Timolol maleate ophthalmic solution, for example, sold under the trademark TIMOPTIC® by Merck, is a non-selective beta-adrenergic receptor blocking agent which is indicated in the treatment of elevated intraocular pressure in patients with ocular hypertension or open-angle glaucoma.

The hypotensive lipids and timolol maleate, when used alone, are effective in treating ocular hypertension. Timolol maleate, when used to control ocular hypertension, may produce one or more disadvantageous side effects, such as headache, fatigue and chest pain, and can have disadvantageous effects on the cardiovascular, digestive, immunologic and nervous systems.

It would be advantageous to provide for effective, preferably enhanced, treatment of ocular hypertension, preferably with reduced side effects from the treatment employed.

SUMMARY OF THE INVENTION

New compositions for and methods of treating ocular hypertension have been discovered. The present invention provides for effective treatment of ocular hypertension often using compositions including reduced concentrations of active components. Such compositions and methods have advantageously been found to be surprisingly effective in treating ocular hypertension and/or to reduce the number and/or frequency and/or severity of unwanted side effects caused by timolol components, e.g., timolol maleate, relative to prior art compositions and methods. The present compositions and methods are relatively straightforward, can be easily produced, for example, using conventional manufacturing techniques, and can be easily and conveniently practiced, for example, using application or administration techniques or methodologies which are substantially similar to those employed with prior compositions used to treat ocular hypertension.

The present methods of treating ocular hypertension comprise applying to an eye an amount sufficient to treat ocular hypertension of a composition comprising a timolol component and a hypotensive lipid component. Each of the timolol component and the hypotensive lipid component is present in the composition in an amount effective to reduce ocular hypertension when applied to a hypertensive eye, that is an eye which has ocular hypertension. The present applying step is effective to treat ocular hypertension, for example, to substantially maintain intraocular pressure or to provide a reduction in intraocular pressure. The present methods preferably provide enhanced treatment of ocular hypertension, for example, enhanced reduction in intraocular pressure, relative to applying a similar composition including either the timolol component or the hypotensive lipid component, but not both, at twice the concentration as in the compositions used in present methods. The present applying step preferably is effective to provide at least one reduced side effect relative to applying a similar composition including the timolol component, but not the hypotensive lipid component, to provide the same treatment of ocular hypertension, e.g., the same reduction in intraocular pressure.

Without wishing to limit the invention to any particular theory or mode of operation, it is believed that the present compositions and methods take advantage of the different modes of action of the timolol component and the hypotensive lipid component. For example, the timolol component alone is effective, when administered to the eye, to decrease the rate of aqueous humor production. On the other hand, the hypotensive lipid component alone is effective, when administered to the eye, to increase the out flow of aqueous humor from the eye. The combination of a timolol component and a hypotensive lipid component is believed to provide both a decreased rate of aqueous humor production and an increased aqueous humor outflow. This combination of active materials is particularly effective in treating ocular hypotension in one or more specific groups of patients, for example, patients with ocular hypotension which effectively responds to both a reduced rate of aqueous humor production and an increase in aqueous humor outflow.

The present timolol component/hypotensive lipid component-containing compositions advantageously provide the same or better reduction in intraocular pressure with reduced concentrations of each of these active materials relative to similar compositions including only the timolol component or the hypotensive component. The reduced concentrations of the active materials in the present compositions also reduce the number and/or severity of side effects, in particular side effects caused by the timolol component.

The timolol component preferably comprises an acid salt of timolol, more preferably comprises timolol maleate. The timolol component is present in the present compositions in an amount effective to reduce intraocular pressure when the composition is applied to a hypertensive eye. The preferred amount of timolol component employed is in a range of about 0.001% to about 1.0% (w/v), more preferably about 0.01% to about 0.2% or about 0.25% or about 0.5% (w/v).

In one embodiment, the hypotensive lipid component has the following formula (I)

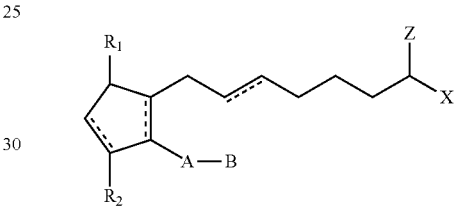

wherein the dashed bonds represent a single or double bond which can be in the cis or trans configuration, A is an alkylene or alkenylene radical having from two to six carbon atoms, which radical may be interrupted by one or more oxide radicals and substituted with one or more hydroxy, oxo, alkyloxy or akylcarboxy groups wherein said alkyl radical comprises from one to six carbon atoms; B is a cycloalkyl radical having from three to seven carbon atoms, or an aryl radical, selected from the group consisting of hydrocarbyl aryl and heteroaryl radicals having from four to ten carbon atoms wherein the heteroatom is selected from the group consisting of nitrogen, oxygen and sulfur atoms; X is a radical selected from the group consisting of —OR$^4$ and —N(R$^4$) 2 wherein R$^4$ is selected from the group consisting of hydrogen, a lower alkyl radical having from one to six carbon atoms,

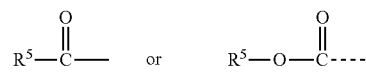

wherein R$^5$ is a lower alkyl radical having from one to six carbon atoms; Z is =O or represents 2 hydrogen radicals; one of R1 and R2 is =O, —OH or a —O(CO)R6 group, and the other one is —OH or —O(CO)R6, or R1 is =O and R2 is H, wherein R6 is a saturated or unsaturated acyclic hydrocarbon group having from 1 to about 20 carbon atoms, or —(CH2) mR7 wherein m is 0 or an integer of from 1 to 10, and R7 is cycloalkyl radical, having from three to seven carbon atoms, or a hydrocarbyl aryl or heteroaryl radical, as defined above, or a pharmaceutically-acceptable salt thereof, provided, however, that when B is not substituted with a pendant heteroatom-containing radical, and Z is =O, then X is not —OR$^4$.

(That is, the cycloalkyl or hydrocarbyl aryl or heteroaryl radical is not substituted with a pendant radical having an atom other than carbon or hydrogen.)

More preferably the hypotensive lipid component has the following formula II:

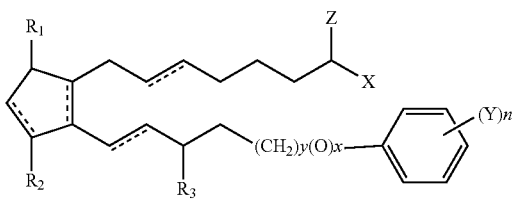

wherein y is 0 or 1, x is 0 or 1 and x and y are not both 1, Y is a radical selected from the group consisting of alkyl, halo, e.g. fluoro, chloro, etc., nitro, amino, thiol, hydroxy, alkyloxy, alkylcarboxy, halo substituted alkyl wherein said alkyl radical comprises from one to six carbon atoms, etc. and n is 0 or an integer of from 1 to about 3 and R3 is =O, —OH or —O(CO)R6 wherein R6 is as defined above. Preferably, n is 1 or 2.

Preferably the hypotensive lipid component has the following formula (III).

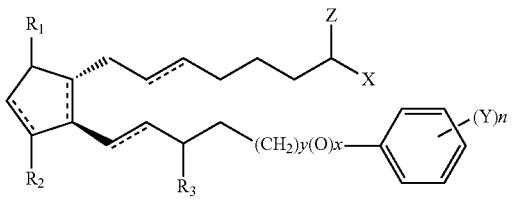

wherein hatched lines indicate α configuration, solid triangles are used to indicate β configuration.

In one embodiment, the hypotensive lipid component has the following formula (IV)

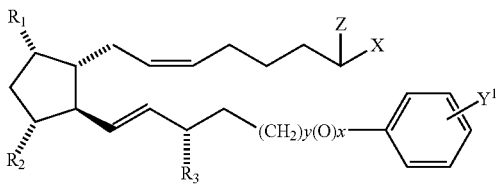

wherein $y^1$ is Cl or trifluoromethyl and the other symbols and substituents are as defined above, in combination with a pharmaceutical carrier.

In a useful embodiment, the hypotensive lipid component has the following Formula (V)

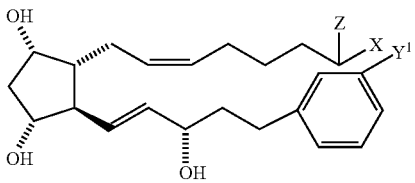

and the 9- and/or 11- and/or 15 esters thereof.

The hypotensive lipid component is present in the present compositions in an amount effective to reduce intraocular pressure when the composition is applied to a hypertensive eye. The preferred amount of hypotensive lipid component employed is in a range of about 0.00001% to about 0.1% (w/v), more preferably about 0.0001% to about 0.01% (w/v).

In a further aspect, the present invention relates to pharmaceutical compositions comprising a therapeutically effective amount of a timolol component, and a therapeutically effective amount of a hypotensive lipid component of formulae (I), (II), (III), (IV) or (V) wherein the symbols have the above meanings, or a pharmaceutically acceptable salt thereof, in admixture with a non-toxic, pharmaceutically acceptable liquid vehicle.

Each and every feature described herein, and each and every combination of two or more of such features, is included within the scope of the present invention provided that the features included in such a combination are not mutually inconsistent.

DETAILED DESCRIPTION OF THE INVENTION

Figure 1:
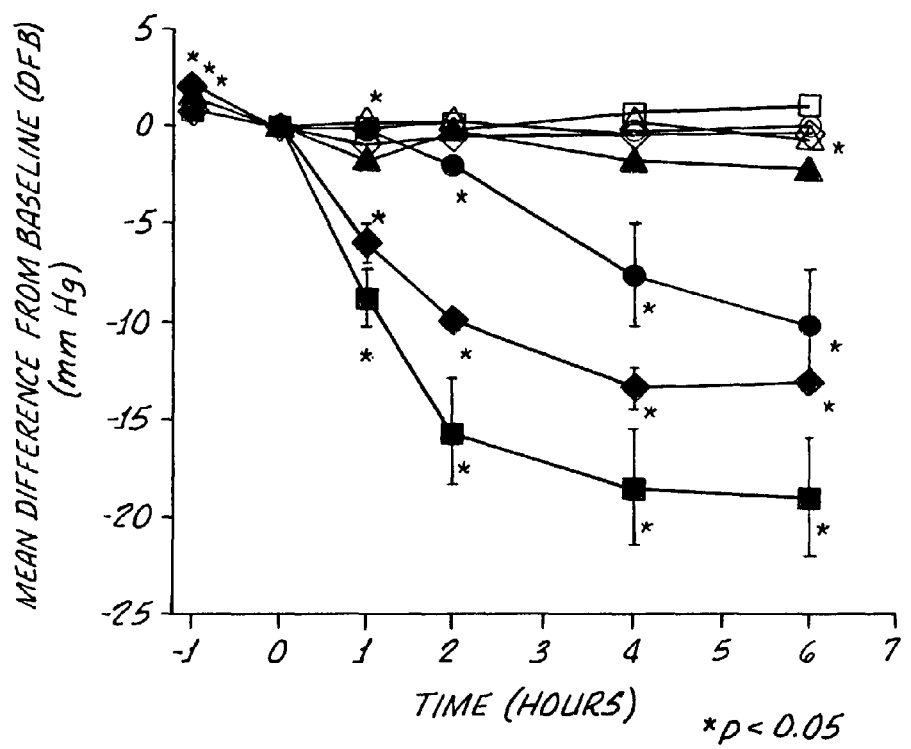
FIG. 1 is a graphical representation of certain effects of a hypotensive lipid/timolol maleate combination on intraocular pressure of laser induced ocular hypertensive cynomolgus monkeys.

The present invention relates to the use of combinations of timolol components and lipid hypotensive components as ocular hypotensives in the treatment of ocular hypertension.

The timolol component is classified as a non-selective beta-adrenergic receptor blocking agent. The chemical name of timolol maleate, a highly preferred timolol component in the present invention, is (–)-1-tert-butylamino)-3-[(4-morpholino-1,2,5-thiodiazol-3 yl)oxyl-2-propanol maleate (1:1) (salt). Other pharmacologically acceptable acid salts may be employed alone or in combination with or without timolol maleate. However, because of its ready availability and its past, known usefulness as an ocular hypotensive, timolol maleate is preferred for use in the present invention. Timolol maleate possesses an asymmetric carbon atom in its structure and preferably is provided as the levo-isomer.

The preferred amount of timolol component employed is in the range of about 0.001% to about 1.0% (w/v); more preferably about 0.0005% or about 0.01% to about 0.2% or about 0.25% or about 0.5% (w/v), based on the amount of timolol present. To illustrate, each mL of a solution containing 0.25% (w/v) contains 2.5 mg of timolol (3.4 mg of timolol maleate).

Currently, Merck sells ophthalmic solutions of timolol maleate (under trademark TIMOPTIC® in concentrations of 0.25% (w/v) and 0.5% (w/v). The present compositions and methods preferably employ concentrations of timolol component which are reduced relative to these commercially available materials. It has been surprisingly found that fully acceptable levels of ocular hypertension treatment are achieved with these reduced concentrations of timolol component in combination with the presently useful hypotensive lipid components, also preferably present at relatively reduced concentrations. The reduced amounts of both timolol component and hypotensive lipid component have surprisingly been found to provide enhanced reduction in intraocular pressure when applied to a hypertensive eye relative to applying a similar composition containing twice as much of one, but not both, of the timolol component and the hypotensive lipid component to the hypertensive eye. The relatively reduced amounts of timolol component and hypertensive lipid component advantageously provide at least one reduced side effect when applied to an eye relative to applying a similar composition including one, but not both, of the timolol component and the hypotensive lipid component to an eye to get the same degree of ocular hypotension treatment, for example, the same degree of reduction of intraocular pressure.

The hypotensive lipid components useful in the present invention are cyclopentane heptanoic acid, 2-cycloalkyl or arylalkyl compounds. These hypotensive lipid components are represented by compounds having the formula I,

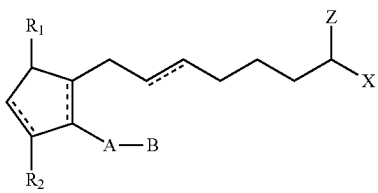

as defined above. The preferred nonacidic hypotensive lipid components used in accordance with the present invention have the following formula (II)

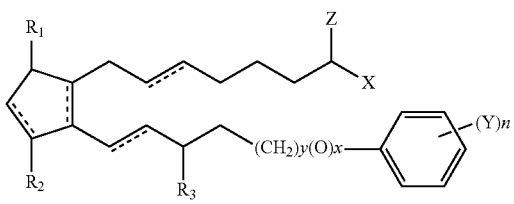

wherein the substituents and symbols are as hereinabove defined.

More preferably the hypotensive lipid components have the following formula (III)

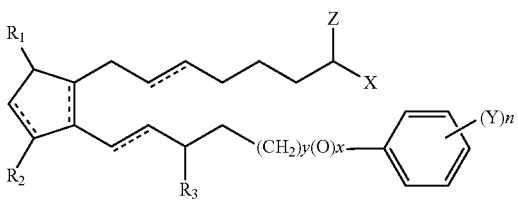

wherein the substituents and symbols are as defined above. More preferably, the hypotensive lipid components utilized in the present invention have the following formula (IV)

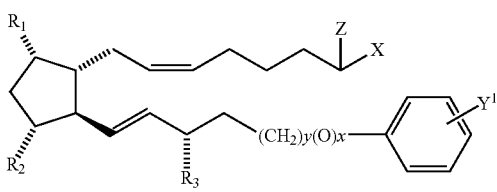

wherein the substituents and the symbols are as defined above.

Still more preferably the present invention utilizes the hypotensive lipid compounds having the following formula (V)

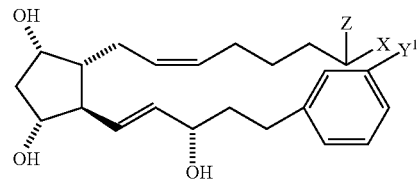

and their 9- and/or 11- and/or 15-esters.

In all of the above formulae (I) to (V) for the hypotensive lipid components, as well as in those provided hereinafter, the dotted lines on bonds between carbons 5 and 6 (C-5), between carbons 13 and 14 (C-13), between carbons 8 and 12 (C-8), and between carbons 10 and 11 (C-10) indicate a single or a double bond which can be in the cis or trans configuration. If two solid lines are used that indicates a specific configuration for that double bond. Hatched lines at positions C-9, C-11 and C-15 indicate the α configuration. If one were to draw the β configuration, a solid triangular line would be used.

In the hypotensive lipid components used in accordance with the present invention, compounds having the C-9 or C-11 or C-15 substituents in the α or β configuration are contemplated. As hereinabove mentioned, in all formulas provided herein broken line attachments to the cyclopentane ring indicate substituents in the α configuration. Thickened solid line attachments to the cyclopentane ring indicate substituents in the β configuration. Also, the broken line attachment of the hydroxyl group or other substituent to the C-11 and C-15 carbon atoms signifies the α configuration.

For the purpose of this invention, unless further limited, the term "alkyl" refers to alkyl groups having from one to about ten carbon atoms, the term "cycloalkyl" refers to cycloalkyl groups having from three to about seven carbon atoms, the term "aryl" refers to aryl groups having from four to about ten carbon atoms. The term "saturated or unsaturated acyclic hydrocarbon group" is used to refer to straight or branched chain, saturated or unsaturated hydrocarbon groups having from one to about 6, preferably one to about 4 carbon atoms. Such groups include alkyl, alkenyl and alkynyl groups of appropriate lengths, and preferably are alkyl, e.g. methyl, ethyl, propyl, butyl, pentyl, or hexyl, or an isomeric form thereof.

The definition of $R_6$ may include a cyclic component, —$(CH_2)_m R_7$, wherein m is 0 or an integer of from 1 to 10, $R_7$ is an aliphatic ring from about 3 to about 7 carbon atoms, or an aromatic or heteroaromatic ring. The "aliphatic ring" may be saturated or unsaturated, and preferably is a saturated ring having 3-7 carbon atoms, inclusive. As an aromatic ring, $R_7$ preferably is phenyl, and the heteroaromatic rings have oxygen, nitrogen or sulfur as a heteroatom, i.e. $R_7$ may be thienyl, furanyl, pyridyl, etc. Preferably m is 0 or an integer of from 1 to 4.

Z is =O or represents two hydrogen atoms.

X may be selected from the group consisting of —$OR^4$ and —$N(R^4)_2$ wherein $R^4$ is selected from the group consisting of hydrogen, a lower alkyl radical having from one to six carbon atoms,

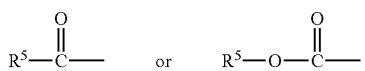

wherein $R^5$ is a lower alkyl radical having from one to six carbon atoms.

Preferred representatives of the hypotensive lipid components within the scope of the present invention are the compounds of formula V wherein X is —OH, i.e. cyclopentane heptenoic acid, 5-cis-2-(3-αhydroxy-4-m-chlorophenoxy-1-trans-butenyl)-3,5-dihydroxy, [1α, 2β, 3α, 5α] and cyclopentane methylheptenoate-5-cis-2(3-αhydroxy-4-m-chlorophenoxy-1-trans-butenyl)-3,5 dihydroxy, [1α, 2α, 3α, 5α] and the 9- and/or 11- and/or 15-esters of this compound. (The numbered designations in brackets refer to the positions on the cyclopentane ring.)

The following hypotensive lipid components may be used in the pharmaceutical compositions and the methods of the present invention.

(1) cyclopentane heptenol-5-cis-2-(3α-hydroxy-5-phenyl-1-trans-pentenyl)-3, 5-dihydroxy, [1α, 2β, 3α, 5α]

(2) cyclopentane heptenamide-5-cis-2-(3α-hydroxy-5-phenyl-1-trans-pentenyl)-3, 5-dihydroxy, [1α, 2β, 3α, 5α]

(3) cyclopentane N,N-dimethylheptenamide-5-cis-2-(3α-hydroxy-5-phenyl-1-trans-pentenyl)-3, 5-dihydroxy, [1α, 2β, 3α, 5α]

(4) cyclopentane heptenyl methoxide-5-cis-2-(3α-hydroxy-5-phenyl-1-trans-pentenyl)-3, 5-dihydroxy, (1α, 2β, 3α, 5α]

(5) cyclopentane heptenyl ethoxide-5-cis-2-(3α-hydroxy-4-meta-chlorophenoxy-1-trans-pentenyl)-3, 5-dihydroxy, [1α, 2β, 3α, 5α]

(6) cyclopentane heptenylamide-5-cis-2-(3α-hydroxy-4-meta-chlorophenoxy-1-trans-pentenyl)-3, 5-dihydroxy, [1α, 2β, 3α, 5α]

(7) cyclopentane heptenylamide-5-cis-2-(3α-hydroxy-4-trifluoromethylphenoxy-1-trans-pentenyl)-3, 5-dihydroxy, [1α, 2β, 3α, 5α]

(8) cyclopentane N-isopropyl heptenamide-5-cis-2-(3α-hydroxy-5-phenyl-1-trans-pentenyl)-3, 5-dihydroxy, [1α, 2β, 3α, 5α]

(9) cyclopentane N-ethyl heptenamide-5-cis-2-(3α-hydroxy-5-phenyl-1-trans-pentenyl)-3, 5 dihydroxy, [1α, 2β, 3α, 5α]

(10) cyclopentane N-methyl heptenamide-5-cis-2-(3α-hydroxy-5-phenyl-1-trans-pentenyl)-3, 5-dihydroxy, [1α, 2β, 3α, 5α]

(11) cyclopentane heptenol-5-cis-2-(3α-hydroxy-4-meta-chlorophenoxy-1-trans-butenyl)-3, 5-dihydroxy, [1α, 2β, 3α, 5α]

(12) cyclopentane heptenamide-5-cis-2-(3α-hydroxy-4-meta-chlorophenoxy-1-trans-butenyl)-3, 5-dihydroxy, [1α, 2β, 3α, 5α]

(13) cyclopentane heptenol-5-cis-2-(3α-hydroxy-5-phenyl-1-trans-pentenyl)3, 5-dihydroxy, [1α, 2β, 3α, 5α]

A pharmaceutically acceptable salt is any salt which retains the activity of the parent compound and does not impart any deleterious or undesirable effect on the subject to whom it is administered and in the context in which it is administered. With regard to the hypotensive lipid components, such salts are those formed with pharmaceutically acceptable cations, e.g., alkali metals, alkali earth metals, etc.

The hypotensive lipid components are present in the present compositions in amounts effective to reduce the intraocular pressure of a hypertensive eye to which the composition is applied. Because of the presence of the active timolol component, the amount of hypotensive lipid component employed preferably is relatively reduced, for example, relative to a composition in which the hypotensive lipid component is the only ocular hypotensive with the same intraocular pressure reduction being achieved. Such reduced amounts of hypotensive lipid components utilized in accordance with the present invention preferably provide a reduction in at least one side effect caused by the presence of the hypotensive lipid component. The preferred amount hypotensive lipid component employed is in the range of about 0.00005% to about 1.0% (w/v), more preferably about 0.0001% to about 0.01% or about 0.1% or about 0.5% (w/v).

Pharmaceutical compositions may be prepared by combining an effective amount of each of a timolol component and a hypotensive lipid component, as active ingredients, with conventional ophthalmically acceptable pharmaceutical excipients, and by preparation of unit dosage forms suitable for topical ocular use.

For ophthalmic application, preferably solutions are prepared using a physiological saline solution as a major vehicle. The pH of such ophthalmic solutions preferably is maintained between about 4.5 and about 8.0 with an appropriate buffer system, a substantially neutral pH being more preferred but not essential. The formulations may also contain conventional, pharmaceutically acceptable preservatives, stabilizers, surfactants and one or more other conventionally used components.

Preferred preservatives that may be used in the pharmaceutical compositions of the present invention include, but are not limited to, benzalkonium chloride, chlorobutanol, thimerosal, phenylmercuric acetate phenylmercuric nitrate, chlorite components, such as stabilized chlorine dioxide, and the like and mixture thereof. A preferred surfactant is, for example, Tween 80. Likewise, various preferred vehicles may be used in the ophthalmic preparations of the present invention. These vehicles include, but are not limited to, polyvinyl alcohol, povidone (polyvinyl pyrrolidone), hydroxypropyl methyl cellulose, poloxamers, carboxymethyl cellulose, hydroxyethyl cellulose, cyclodextrin and purified water and combinations or mixtures thereof.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers, borate buffers and the like and mixtures thereof. Acids or bases may be used to adjust the pH of these formulations as needed.

In a similar vein, an ophthalmically acceptable antioxidant component may be included in the present composition. Such antioxidant components include, but are not limited to, sodium metabisulfite, sodium thiosulfate, acetylcysteine, butylated hydroxyanisole, butylated hydroxytoluene, and the like and mixtures thereof.

Other excipient components which may be included in the ophthalmic preparations include, without limitation, chelating agents. The preferred chelating agent is EDTA disodium, although other chelating agents may be used in place of or in conjunction with it.

The ingredients are usually in the following amounts:

| Ingredients | Amount (w/%) |
|---|---|
| Timolol Component | about 0.001–1 |
| Hypotensive Lipid Component | about 0.00005–1 |
| Preservative | 0–0.10 |
| Vehicle | 0–40 |
| Tonicity adjustor | 0–10 |
| Buffer | 0.01–10 |
| pH adjustor | q.s. pH 4.5–7.5 |
| antioxidant | as needed |
| surfactant | as needed |
| purified water | as needed to make 100% |

The actual doses of the timolol component and hypotensive lipid component used depends on the specific compounds, being employed on the specific condition resulting in the ocular hypertension being treated, on the severity and duration of the ocular hypertension being treated, and the like factors. In general, the selection of the appropriate doses is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses.

Especially preservative-free solutions are often formulated in non-resealable containers containing up to about ten, preferably up to about five units doses, where a typical unit dose is in the range of one to about 8 drops, preferably one to about 3 drops. The volume of one drop usually is about 20-35 ul (microliters).

The invention is further illustrated by the following non-limiting Examples.

EXAMPLES

Intraocular pressure studies were performed in conscious cynomolgus monkeys, trained to accept pneumatonometry. The animals were restrained for pneumatonometry in custom-designed chairs and given fruit during the experiment.

A series of four (4) compositions were prepared, by blending the ingredients together. These compositions were as follows:

| Ingredient | Compositions (A) | | | |
|---|---|---|---|---|
|  | 1 | 2 | 3 | 4 |
| Hypotensive lipid (B) | 0.001% (w/v) | — | 0.001% (w/v) | — |
| Timolol Maleate | — | 0.05% w/v | 0.005% (w/v) | — |
| Polysorbate 80 | 0.01 (w/v) | 0.1% (w/v) | 0.1% (w/v) | 0.1% (w/v) |
| Tris Hcl | 10 mM | 10 mM | 10 mM | 10 mM |

A. Each composition had a pH of about 7.4 and was an aqueous solution including 0.9% (w/v) of sodium chloride.

B. The hypotensive lipid was: cyclopentane N-ethyl heptenamide-5-cis-2-(3α-hydroxy-5-phenyl-1-trans-pentenyl)-3, 5-dihydroxy, [1α, 2β, 3α, 5α].

The treatments, coded to the experimenter, were applied topically to the glaucomatous eye as a single 25 μl volume drop, and the normotensive fellow eye received 25 μl of normal saline. The solutions were administered at time 0. Proaracaine (0.1%) was used to provide corneal anesthesia for the intraocular pressure measurements that were performed at one hour before dosing, just before dosing, and then 1, 2, 4 and 6 hours thereafter.

The mean intraocular pressure (IOP) values for the glaucomatuous eyes at time 0 were 40.5 mm Hg for the Composition 1 group, 38.8 mm Hg for the Composition 2 group, 40.6 mm Hg for the Composition 3 group and 39.5 mm Hg for the Composition 4 group.

IOP mean differences from baseline (DFB) for treated eyes (test DFB) and fellow eyes (fellow DFB) are depicted in FIG. 1. Test DFB values were statistically significant for the following groups (Student's t-test for paired samples):

| Compositions | Range (mm Hg), $p < 0.05$ |
|---|---|
| 1 | −2.0 to −10.3 |
| 2 | +2.1 to −13.4 |
| 3 | +2.0 to −19.0 |
| 4 | +1.0 to −2.3 |

Figure 2:
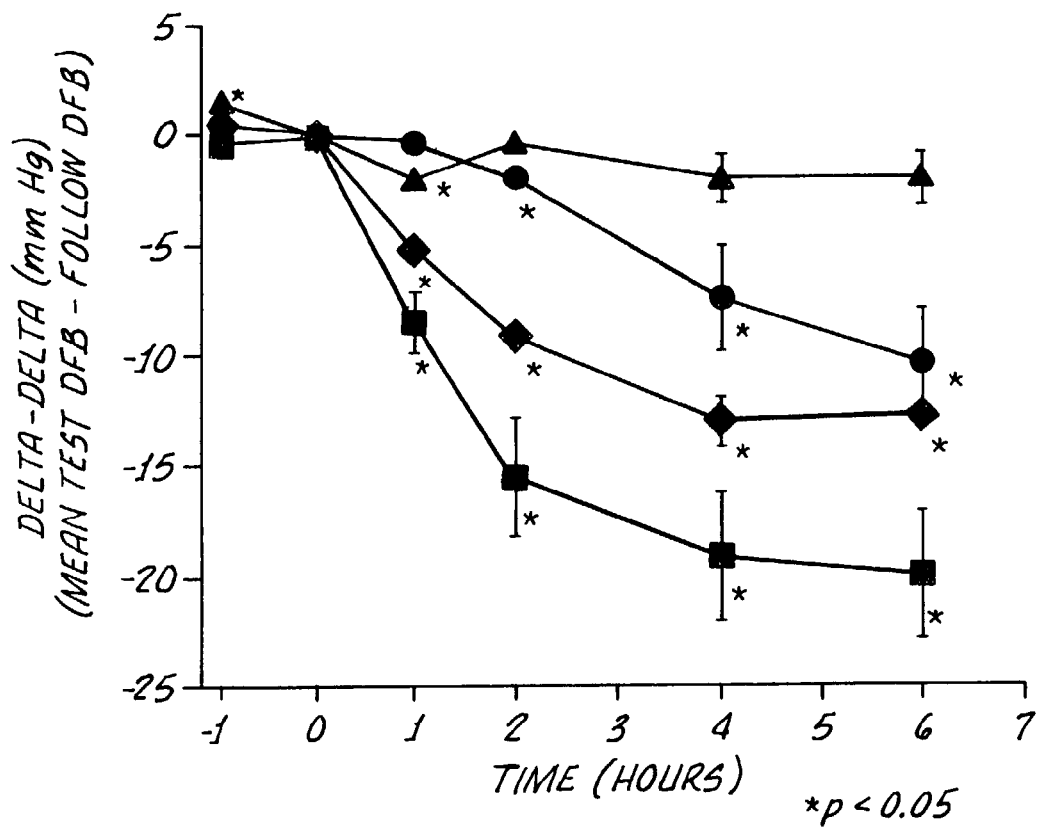
FIG. 2 is a graphical representation of certain other effects of a hypotensive lipid/timolol maleate combination on intraocular pressure of laser induced ocular hypertensive cynomolgus monkeys.

The effects of combination treatment with the hypotensive lipid and the timolol component (Composition 3) on IOP of glaucomatous monkeys were compared to each of the other treatments alone (Student's t-test for unpaired samples, p<0.05). The delta-delta values (test DFB—fellow DFB) for the combination treatment (Composition 3) group were significantly lower than those for the hypotensive lipid alone (composition 1) (time =1, 2, 4, 6 hr). The delta-delta values are depicted in FIG. 2.

The combination treatment (Composition 3) using relatively low doses of hypotensive lipid and timolol maleate was surprisingly found to be more efficacious in reducing IOP than treatments with either only one of these materials (Compositions 1 and 2) or none of these materials (Composition 4).

While this invention has been described with respect to various specific examples and embodiments, it is to be understood that the invention is not limited thereto and that it can be variously practiced within the scope of the following claims.

What is claimed is:

1. A composition comprising 0.5% (w/v) timolol and 0.03% (w/v) of cyclopentane N-ethyl heptenamide-5-cis-2-(3α-hydroxy-5-phenyl-1-trans-pentenyl)-3,5-dihydroxy, [1α,2β,3α,5α] which is effective in reducing ocular hypertension when applied to a hypertensive eye.

2. A composition comprising 0.5% (w/v) timolol and 0.03% (w/v) of cyclopentane N-ethyl heptenamide-5-cis-2-(3α-hydroxy-5-phenyl-1-trans-pentenyl)-3,5-dihydroxy [1α,2β,3α,5α] said composition when applied to an eye being effective to treat ocular hypertension and being in the form of a solution.

3. The composition of claims 1 and 2 wherein the composition comprises timolol maleate.

4. The composition of claims 1 and 2 further comprising benzalkonium chloride as a preservative.

* * * * *

UNITED STATES PATENT AND TRADEMARK OFFICE
CERTIFICATE OF CORRECTION

PATENT NO. : 8,629,140 B2
APPLICATION NO. : 10/153043
DATED : January 14, 2014
INVENTOR(S) : June Chen et al.

Page 1 of 2

It is certified that error appears in the above-identified patent and that said Letters Patent is hereby corrected as shown below:

On the title page, in item (56), under "OTHER PUBLICATIONS", in column 2, line 27, delete "Stucture" and insert -- Structure --, therefor.

In the Specification

In column 1, line 58, delete "b-adrenoreceptor" and insert -- β-adrenoreceptor --, therefor.

In column 2, line 45, delete "3U.S." and insert -- U.S. --, therefor.

In column 4, line 40, delete "akylcarboxy" and insert -- alkylcarboxy --, therefor.

In column 4, lines 52-53, delete " $R^5-O-\overset{\overset{O}{\|}}{C}\cdots$ " and insert -- $R^5-O-\overset{\overset{O}{\|}}{C}-$ --, therefor.

In column 6, line 41, delete "3 yl)" and insert -- 3-yl) --, therefor.

In column 6, line 41, delete "oxyl-2-propanol" and insert -- oxy]-2-propanol --, therefor.

In column 6, line 50, delete "(w/v);" and insert -- (w/v), --, therefor.

In column 7, lines 46-52, delete " 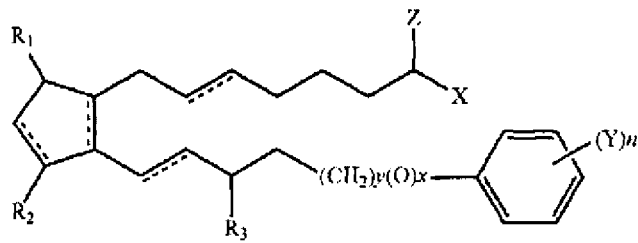 " and

Signed and Sealed this
Twentieth Day of January, 2015

Michelle K. Lee
*Deputy Director of the United States Patent and Trademark Office* insert -- 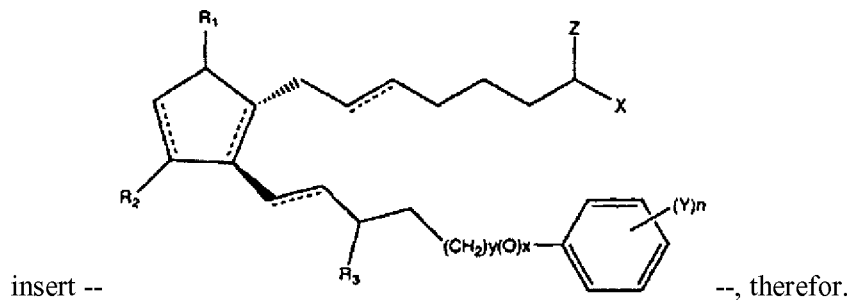 --, therefor.

In column 8, line 34, delete "a" and insert -- α --, therefor.

In column 9, line 14, delete "3,5 dihydroxy," and insert -- 3,5-dihydroxy, --, therefor.

In column 12, line 8, delete "Proaracaine" and insert -- Proparacaine --, therefor.

In column 12, lines 12-13, delete "glaucomatuous" and insert -- glaucomatous --, therefor.

In the Claims

In column 12, line 56, in claim 2, delete "(360 -hydroxy" and insert -- (3α-hydroxy --, therefor.

In column 12, line 56, in claim 2, delete "dihydroxy" and insert -- dihydroxy, --, therefor.